United States Patent
Sukegawa et al.

(10) Patent No.: US 7,997,129 B2
(45) Date of Patent: Aug. 16, 2011

(54) DEVICE AND METHOD FOR GENERATING REFERENCE GEOMETRIC DATA FOR TIRE INSPECTION

(75) Inventors: Tetsuya Sukegawa, Kodaira (JP); Takao Kokubu, Akishima (JP)

(73) Assignee: Bridgestone Corporation, Tokyo (JP)

( * ) Notice: Subject to any disclaimer, the term of this patent is extended or adjusted under 35 U.S.C. 154(b) by 102 days.

(21) Appl. No.: 12/309,411

(22) PCT Filed: Jul. 23, 2007

(86) PCT No.: PCT/JP2007/064467
§ 371 (c)(1),
(2), (4) Date: Jun. 12, 2009

(87) PCT Pub. No.: WO2008/010594
PCT Pub. Date: Jan. 24, 2008

(65) Prior Publication Data
US 2009/0272183 A1   Nov. 5, 2009

(30) Foreign Application Priority Data

Jul. 21, 2006 (JP) .................................. 2006-199414

(51) Int. Cl.
B60C 23/02 (2006.01)
(52) U.S. Cl. ..................................... 73/146.5
(58) Field of Classification Search .................. None
See application file for complete search history.

(56) References Cited

U.S. PATENT DOCUMENTS

| 5,789,668 A * | 8/1998 | Coe et al. ................... 73/146 |
| 6,124,925 A | 9/2000 | Kaneko et al. |
| 6,615,650 B2 * | 9/2003 | Mahner ....................... 73/146 |
| 7,177,740 B1 * | 2/2007 | Guangjun et al. ............... 701/34 |
| 2001/0052259 A1 * | 12/2001 | Mahner ....................... 73/146 |
| 2005/0058333 A1 | 3/2005 | Kaneko et al. |
| 2007/0204684 A1 * | 9/2007 | Muhlhoff et al. ............... 73/146 |
| 2007/0209431 A1 * | 9/2007 | Fujisawa et al. ............... 73/146 |
| 2010/0180676 A1 * | 7/2010 | Braghiroli et al. ............... 73/146 |

FOREIGN PATENT DOCUMENTS

| JP | A 10-115508 | 5/1998 |
| JP | A 11-138654 | 5/1999 |
| JP | A 2003-240521 | 8/2003 |
| JP | A 2005-331274 | 12/2005 |

* cited by examiner

*Primary Examiner* — Andre J Allen
(74) *Attorney, Agent, or Firm* — Oliff & Berridge, PLC

(57) ABSTRACT

A split mold for vulcanizing a tire is held at a mold holding section, which is held on a rotatable base, and then a measuring section measures distances to an inner surface of the split mold in the inside diameter direction and in the axial direction. An operating section acquires two-dimensional geometric data of the inner surface of the split mold from the distances measured above, and further acquires geometric data over the entire circumference by rotating the rotatable base, and the data are combined to acquire three-dimensional geometric data of the inner surface of the split mold and make reference geometric data for tire inspection.

5 Claims, 4 Drawing Sheets

DEVICE AND METHOD FOR GENERATING REFERENCE GEOMETRIC DATA FOR TIRE INSPECTION

TECHNICAL FIELD

The present invention relates to a device and a method for generating reference geometric data for tire inspection that is used for inspecting a geometric of bulged/dented markings formed on a tire surface.

RELATED ART

As a method for inspecting bulged/dented markings formed on a tire surface, known is an inspection method comprising irradiating a tire surface on which the bulge and dent are formed with light, taking an image of bright lines on the tire surface formed by the light with an imaging camera, loading image data corresponding to the bulged/dented markings, and conducting a process of comparing the image data with pre-stored image data of bulged/dented markings to examine whether the bulges and dents are appropriately presented at a given position in a given shape (see, for example, JP 10115508 A).

DISCLOSURE OF THE INVENTION

The above-mentioned conventional method for tire inspection needs reference geometric data for tire inspection, which can be a reference of determination, for not only inspecting existence or nonexistence and arrangement of bulged/dented markings formed on a tire surface but also inspecting geometry of the markings, i.e., determining existence or nonexistence of defection of three-dimensional geometry as well as determining a location, degree or the like of geometry defects. The reference geometric data for tire inspection is, however, generated by taking out the marking parts from image information that is derived from an actual measurement of tire appearances, so that the data is affected by innate characteristics of the measuring device such as resolution, accuracy, field of vision, blind side, and contains positional errors occurring in each measurement, whereby fluctuation cannot be avoided.

Tires which are selected for generating the reference geometric data for tire inspection also have fluctuations and do not always have the center value of the standard even when the tires are within the standard. Therefore, it is difficult to generate reference geometric data for tire inspection from data of a tire having center values of the standard.

Furthermore, this inspection method measures actual tires and thus has a problem in precision because the tire has burrs and deformations. In addition, it needs a lot of manual reworks.

The present invention has been made in view of the above-mentioned problems. The present invention aims to provide a device and a method for generating reference geometric data for tire inspection that do not involve fluctuations and are precise and do not need the manual reworks.

For achieving the aims described above, a device for generating reference geometric data for tire inspection according to the invention comprises mold holding means for holding a split mold for vulcanizing a tire, measuring means for measuring distances to an inner surface of the split mold in the inside diameter direction and in the axial direction, a rotatable base for carrying and rotating the mold holding means, and computing means for generating reference geometric data for tire inspection by acquiring two-dimensional geometric data of the inner surface of the split mold from the distances measured by the measuring means, additionally acquiring geometric data of the inner surface of the split mold over the entire circumference while rotating the rotatable base, and combining the data to acquire three-dimensional geometric data of the inner surface of the split mold.

A device for generating reference geometric data for tire inspection according to the invention comprises a fixing base for carrying a split mold for vulcanizing a tire, measuring means for measuring distances to an inner surface of the split mold in the inside diameter direction, computing means for generating data for tire inspection by acquiring two-dimensional geometric data of the inner surface of the split mold over the entire circumference from the distances measured by the measuring means while rotating the measuring means, additionally acquiring two-dimensional geometric data of the inner surface of the split mold over the entire circumference across the split mold in the axial direction, and combining the data to acquire three-dimensional geometric data of the inner surface of the split mold.

A method for generating reference geometric data for tire inspection according to the invention comprises the steps of placing a split mold for vulcanizing a tire on a rotatable base to center of the split mold, measuring distances to an inner surface of the split mold in the inside diameter direction and in the axial direction, acquiring two-dimensional geometric data of the inner surface of the split mold from the distances thus measured, further acquiring geometric data over the entire circumference by rotating the rotatable base, and generating reference geometric data for tire inspection by further acquiring geometric data of the inner surface of the split mold over the entire circumference while rotating the rotatable base, and combining the data to acquire three-dimensional geometric data of the inner surface of the split mold.

A method for generating reference geometric data for tire inspection according to the invention comprises the steps of placing a split mold for vulcanizing a tire on a rotatable base to center of the split mold, measuring distances to an inner surface of the split mold over the entire circumference across the split mold in the inside diameter direction, acquiring two-dimensional geometric data of the inner surface of the split mold over the entire circumference from the distances thus measured, generating reference geometric data for tire inspection by further acquiring two-dimensional geometric data of the inner surface of the split mold over the entire circumference across the split mold in the axial direction, and combining the data to acquire three-dimensional geometric data of the inner surface of the split mold.

According to the invention, a geometry of the inner surface of the split mold for vulcanizing a tire, instead of measuring a surface of an actual tire, is directly measured, so that reference geometric data for tire inspection can be generated accurately and efficiently, enabling more advanced tire appearance inspection. In addition, an actual tire is not measured, so that manual reworks are not needed. Moreover, reference geometric data for tire inspection can be generated without a design drawing of a tire.

BEST MODE FOR CARRYING OUT THE INVENTION

Prior to describing a device for generating reference geometric data for tire inspection according to the invention, a tire appearance inspection device is firstly described which uses the reference geometric data for tire inspection generated according to the method of the invention.

Figure 1:
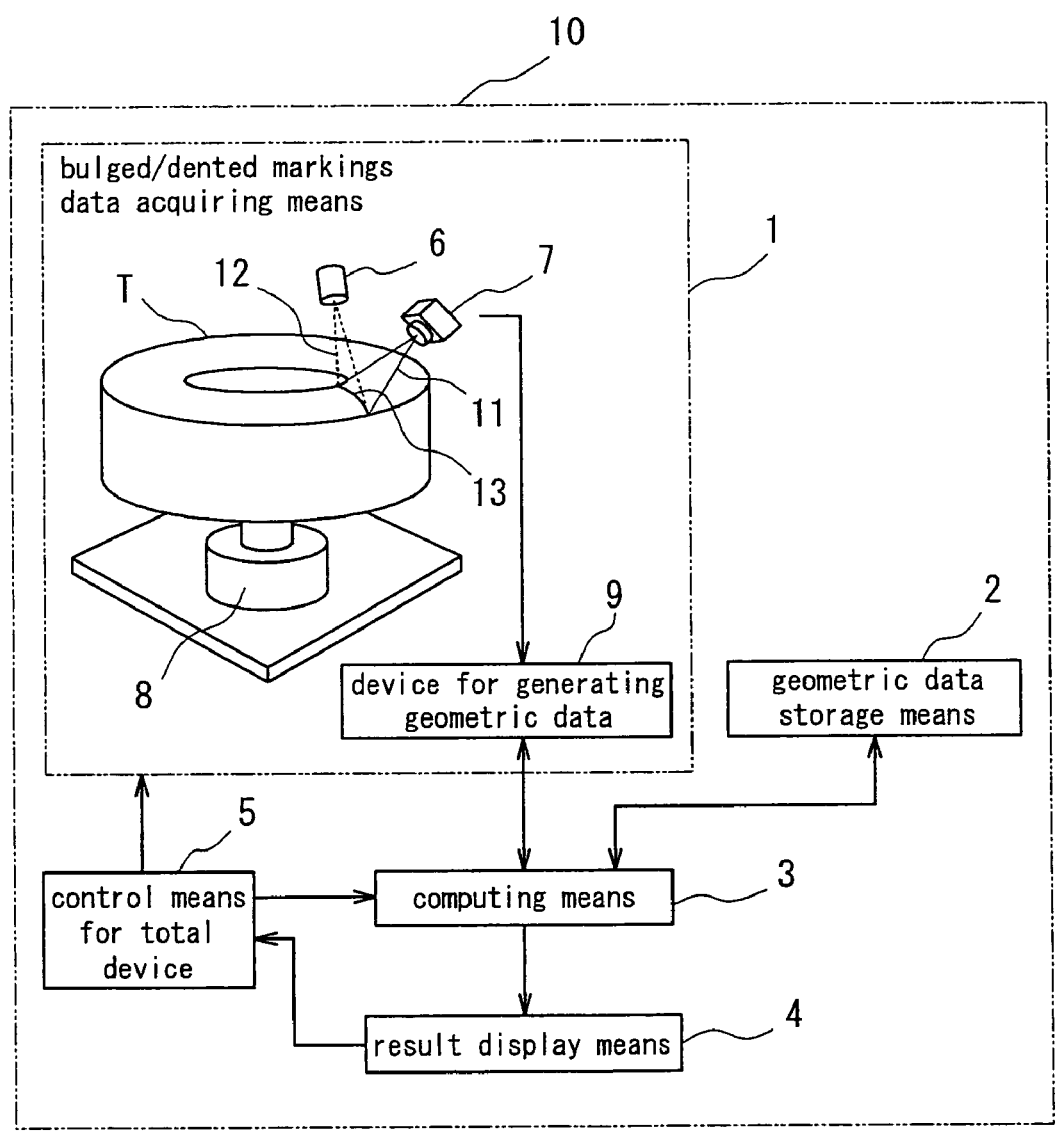
FIG. 1 is a block diagram showing a tire appearance inspection device for inspecting three-dimensional geometry of bulged/dented markings formed on a tire surface.

FIG. 1 is a block diagram showing a tire appearance inspection device for inspecting three-dimensional geometry of bulged/dented markings formed on a tire surface. The tire appearance inspection device 10 comprises bulged/dented data acquisition means 1 for acquiring data of distribution of bulged/dented markings in a given tire surface portion, markings data storing means 2 for storing markings data which become templates of respective markings (reference geometric data for tire inspection) and information of arrangements of the markings, computing means 3 for specifying a tire surface portion corresponding to the markings on the basis of the bulged/dented markings data acquisition means 1 and the marking data input from the marking data storing means 2 to determine whether or not the three-dimensional geometry of the markings is appropriate on the basis of a consistency between the bulged/dented markings distribution data of the specified tire surface portions and the data of the bulged/dented markings data, result display means 4 for outputting a determined result of the passing state, and whole device control means 5 for controlling these means.

The bulged/dented markings data acquiring means 1 comprises a semiconductor laser 6 for emitting a flat beam (sheet light) 12 which spread like a fan, a two-dimensional camera 7 for taking a image of bright lines 13 formed on a surface of the tire T by the sheet light 12, a tire rotation driving device 8 for rotating the tire at a given rotation rate or indexing a tire in the circumferential direction by a given pitch, a geometric data creating device 9 for inputting image data from the camera 7 taken at a given interval in a circumferential direction of tire, and extracting only the bright lines 13 from respective image data to generate the three-dimensional bulged/dented markings distribution data over the entire area of an annular surface area of the tire based on these bright lines 13. Meanwhile, a numeral 11 designates a visual field of a camera.

A method of generating a profile of work (three-dimensional geometric data) by gathering the images of bright lines formed on the work under such a condition that the work is irradiated with the sheet light while transferring is generally referred to as a light-section method. In the bulged/dented markings data acquiring means 1 according to this embodiment, the three-dimensional geometric data can be accurately acquired directly from the taken images by use of the light-section method.

The markings data storing means 2 stores markings data (reference geometric data for tire inspection).

Moreover, the markings data storing means 2 stores the marking data as well as the arrangement position information of the markings with respect to the tire to be examined. The arrangement position information is collected from specs relating to the center position of the marking on the annular tire surface area.

Computing means 3 comprises the steps of: acquiring the bulged/dented marking distribution data about each area component in a given tire surface area including the markings from the bulged/dented data acquisition means 1, on the basis of a command from the control means for overall apparatus 5, acquiring the marking data and the marking arrangement information which are preliminarily prepared from the marking data storing means 2, setting a search area in the tire surface area, on the basis of the marking arrangement information which are preliminarily prepared with respect to the markings, changing a position of the tire surface portion, which is to be corresponding to the markings in the search area, specifying the tire surface portion at which consistency between the bulged/dented markings distribution data of the tire surface portion and the data of the markings, which are calculated at respective positions is largest as the portion corresponding to the markings, measuring the consistency between the bulged/dented markings distribution data of the specified tire surface portion and the data of the figure model, with respect to the markings, and determining whether or not the three-dimensional shape of the markings is accepted on the basis of the consistency mentioned above.

The device for generating reference geometric data for tire inspection according to the invention generates the above-mentioned marking data (reference geometric data for tire inspection) on the basis of molds (vulcanization dies) for forming the tire. Since the mold have no geometric fluctuation, the method of generating reference geometric data according to the invention can generate accurate reference geometric data for tire inspection without fluctuation.

Figure 2:
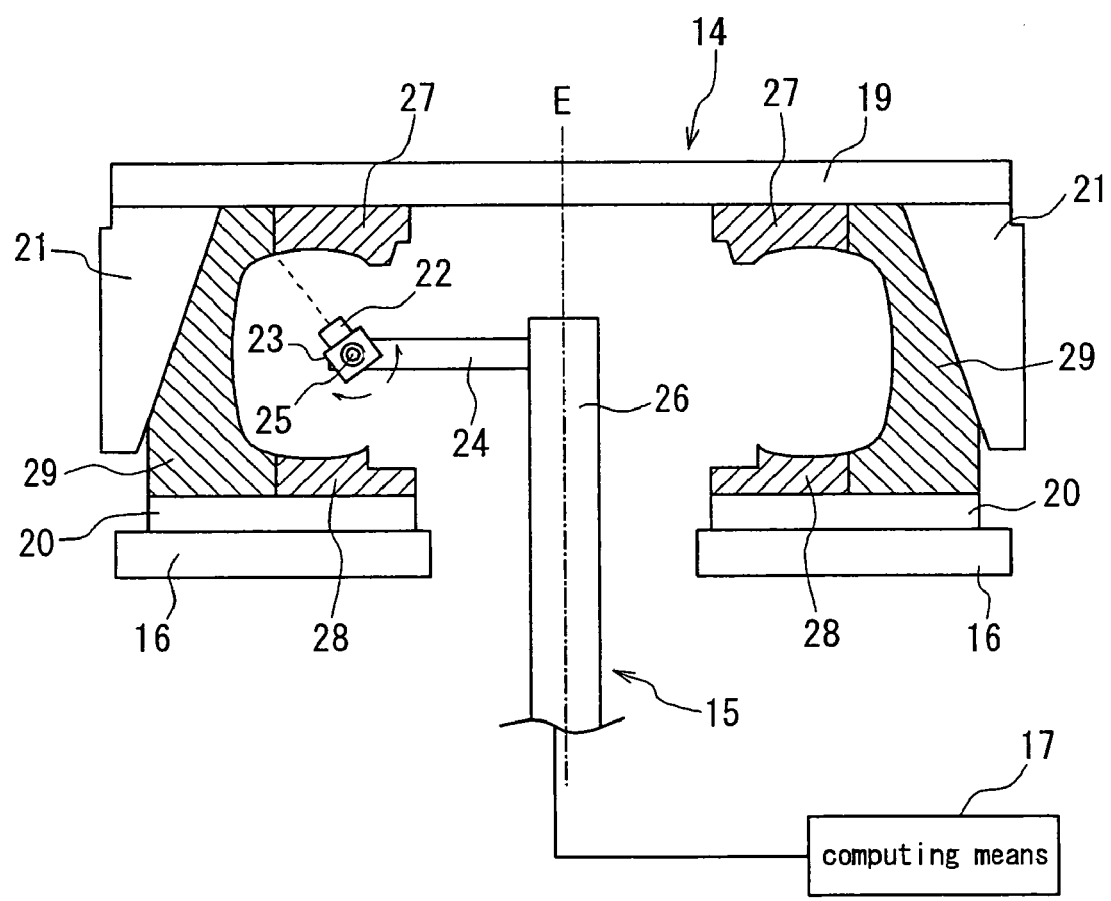
FIG. 2 is a cross-sectional view schematically showing a principle and a constitutional example of a device for generating reference geometric data for tire inspection according to a first embodiment.

In the next, first embodiment of the device for generating reference geometric data for tire inspection according to the invention will be explained in detail. FIG. 2 is a cross-sectional view schematically showing a principle and constitutional examples of the device for generating reference geometric data for tire inspection of the first embodiment. The device for generating reference geometric data for tire inspection is comprises mold holding means 14 for holding a split mold for vulcanizing a tire, measuring means 15 for measuring distances to an inner surface of the split mold in the inside diameter direction and in the axial direction, a rotatable base 16 for carrying and rotating the mold holding means 14, and computing means 17 for processing values measured by the measuring means 15.

The mold holding means 14 comprises a top plate 19 in a planar shape, a bottom plate 20 in a planar ring shape, and holding means 21. The split mold to be measured by the measuring device comprises upper and lower side molds 27, 28 in a ring shape, and a segment mold 29 divided into pieces in radial direction of the mold. The upper side mold 27 is fixed on the top plate 19 and the lower side mold 28 is fixed on the bottom plate 20. The holding means 21 has a downwardly expanding tapered shape in the inner circumference surface. When the holding device 21 descends (moves to the bottom plate 20 side), its tapered surface pushes the divided segment mold 29 against a shaft center side of the split mold and the mold is closed. E represents a shaft center of the mold.

The measuring means 15 comprises a support pedestal 23 at one end of the support arm 24, the support pedestal 23 comprises a non-contact laser displacement gauge 22 attached so that a laser beam is emitted toward the inner surface of the split mold. The laser displacement gauge 22 can freely rotate about a rotation axis 25 of the support pedestal 23. The other end of the support arm 24 is fixed on an arm support pedestal 26. The laser displacement gauge 22 emits a laser beam toward the inner surface of the split mold, and receives a reflected beam to measure the distance to an irradiated matter. The support arm 24 can be exchanged according to the size of the split mold. This makes possible it to measure the geometry of the split mold regardless of the size of the split mold. The arm support pedestal 26 has a cylindrical shape, and is fixed on a pedestal (not shown) so that a shaft center of the arm support pedestal 26 agrees with that of the split mold after the split mold is centered.

The rotatable base 16 is so configured that it is driven by a servomotor (not shown) through a belt (not shown), it rotates the mold holding means 14 at given rotation rate or transfers it pitch by pitch in a circumferential direction by a given pitch according to a distance between the laser displacement gauge 22 and an irradiated matter.

Figure 3:
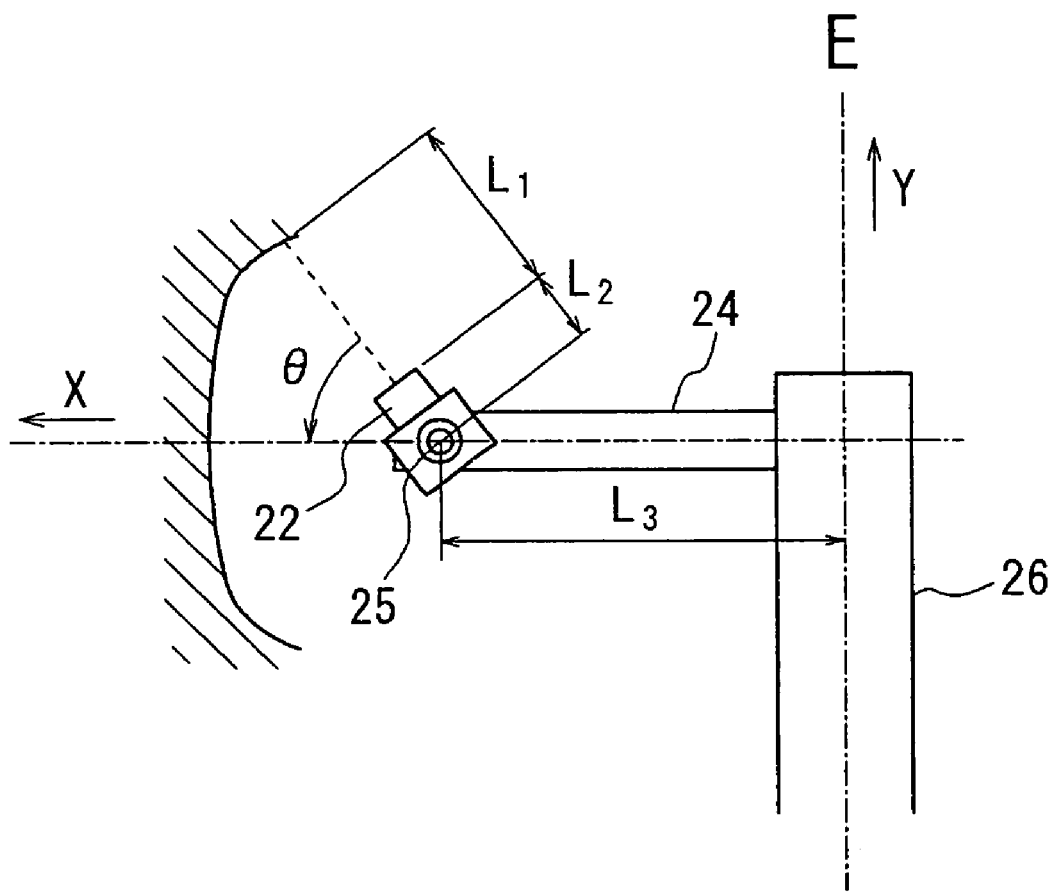
FIG. 3 is an illustrative drawing showing a method for measuring a distance to an inner surface of the split mold.

The computing means 17 calculates a cross-sectional shape of the mold from data measured by the measuring means 15. FIG. 3 illustrates a method for measuring a distance to an inner surface of the split mold. At first, assuming a direction of inner diameter (the axial direction of the support arm) is x-axis, a direction of a shaft center E is y-axis, a position of intersection of x-axis and y-axis is a reference position (0, 0). Further, assuming the laser displacement gauge 22 rotates θ degree with respect to x-axis about the rotation axis 25, a distance to a measuring point on the inner surface of the split mold measured by the laser displacement gauge 22 is L1, a distance from the laser displacement gauge 22 to the rotation axis 25 is L2, and a distance from the rotation axis 25 to the mold shaft center E is L3. If L2 and L3 are known and the laser displacement gauge 22 is able to measure the distance L1, which is the distance to the measuring point on the inner surface of the split mold, a distance to the measuring point on the inner surface of the split mold in the x-axis direction can be calculated from $(L1+L2)\cos\theta+L3$ and a distance to that in y-axis direction can be calculated from $(L1+L2)\sin\theta$.

The computing means 17 acquires two-dimensional cross sectional geometric data of the mold from distances to the inner surface of the split mold in the x-axis direction (the inner diameter direction) and in the y-axis direction (the shaft center E direction) measured by the laser displacement gauge 22 at respective given angles. Additionally, the rotatable base 16 is rotated to rotate the mold holding means 14, and geometric data of the mold section at given intervals in the circumferential direction are acquired, and the acquired two-dimensional cross sectional geometric data over the entire circumference (360 degree) are processed and combined to acquire the three-dimensional geometry (heights of the bulge and dent) data over the entire circumference of one tire.

Moreover, an accurate three-dimensional geometric data is made by calculating and correcting fluctuations of centering the rotatable base and an angular difference between each layer from deviations of total cross sectional geometric data. Finally, by using the acquired data, reference geometric data for tire inspection for designs of a tire side portion, tread patterns of a tire crown portion and the like are made.

Figure 4:
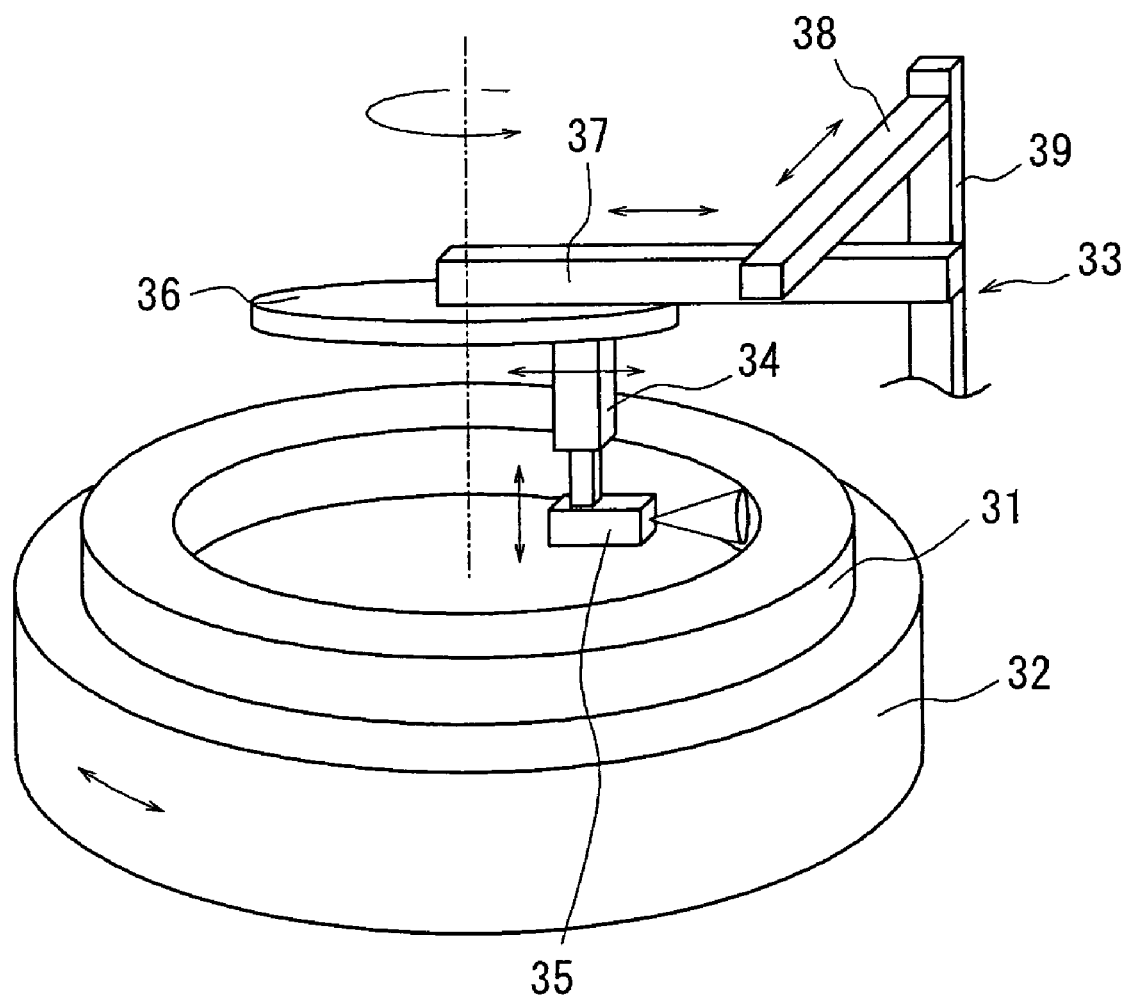
FIG. 4 is a perspective view schematically showing a device for generating reference geometric data for tire inspection according to a second embodiment.

Next, a second embodiment of a device for generating reference geometric data for tire inspection according to the invention will be explained. FIG. 4 is a perspective view schematically showing a device for generating reference geometric data for tire inspection according to the second embodiment. The device for generating reference geometric data for tire inspection comprises a fixing base 32 for holding a split mold 31 for vulcanizing a tire, measuring means 33 for measuring distances to an inner surface of the split mold 31 in the inside diameter direction, and computing means (not shown) for processing the measured values from the measuring means 33.

The measuring means 33 is provided with a non-contact laser displacement gauge 35 attached on one end of a support arm 34 to emit a laser beam toward the inner surface of the split mold 31. The laser displacement gauge 35 emits a laser beam toward the inner surface of the split mold, and receives a reflected beam to measure distances to the irradiated objects. A rotatable plate 36 can rotate 360 degrees and the laser displacement gauge 35 rotates with the rotation of the rotatable plate. Additionally, the support arm 34 has a variable length. The other end of the support arm 34 can be displaced to a position which decenters from the rotation center of the rotatable plate 36 and measurements can be conducted with a constant distance to an inner surface of the split mold by rotating the rotatable plate 36. This makes it possible to measure the geometry of the split mold without a limitation of a size of the split mold.

The rotatable plate 36 is attached on an x-axis arm 37, and the x-axis arm 37 is attached on a y-axis arm 38. The y-axis arm 38 is fixed on an arm support base 39 and the arm support base 39 is fixed on a pedestal (not shown). Lengths of the x-axis arm 37 and the y-axis arm 38 are variable.

In the measurement, the measuring means 33 firstly rotates the plate 36 upon receiving an order of centering while emitting a laser beam to the inner surface of the split mold 31, and measures distances from the laser displacement gauge 35 to the inner surface of the split mold 31 at 0 degree, 90 degrees, 180 degrees, and 270 degrees. Then, the lengths of the x-axis arm 37 and the y-axis arm 38 are changed to center the split mold 31, and the axial center of the split mold 31 and the rotation center of the rotatable plate 36 are aligned.

Subsequently, the measuring means 33 measures distances from the laser displacement gauge 35 to the inner surface of the split mold 31 while rotating the rotatable plate 36 for 360 degrees. The computing means 17 acquires geometric data of the inner surface of the split mold 31 over the entire circumference (360 degrees) from a measured distance to the inner surface of the split mold 31. Thereafter, the length of the support arm 34 is changed and the computing means 17 acquires two-dimensional cross sectional geometric data of the inner surface of the split mold 31 of over the entire circumference (360 degrees) in the direction of the axial center of the split mold 31, and processes and combines the acquired two-dimensional cross sectional geometric data to acquire the three-dimensional geometry (heights of the bulge and dent) data over the entire circumference of one tire.

Moreover, an accurate three-dimensional geometric data is made by correcting fluctuations of centering from deviations of total geometric data. Finally, reference geometric data for tire inspection for design of a tire side portion and tread patterns of a tire crown portion are made by using the acquired data.

Although the measurement is conducted with fixing the split mold 31 on the fixing base 32 and rotating the laser displacement gauge 35 (the rotatable plate 36) in the second embodiment, the split mold 31 may be rotated with fixing the laser displacement gauge 35 (the rotatable plate 36) when the split mold 31 is light in weight.

Additionally, although the distance to the irradiated matter is measured by means of the laser displacement gauge in the first and second embodiments, the distance to the irradiated matter may be determined by processing the data which are taken by a high-speed camera.

The invention claimed is:

1. A device for generating reference geometric data for inspecting a tire by measuring a split mold, comprising:
a mold holder that holds the split mold for vulcanizing a tire,
a measuring device that measures distances to an inner surface of the split mold in an inside diameter direction and in an axial direction, a rotatable base that carries and rotates the mold holder, and a computing device that generates data used in tire inspection by acquiring two-dimensional geometric data of the inner surface of the split mold from the distances measured by the measuring device, additionally acquiring geometric data of the inner surface of the split mold over an entire circumference while rotating the rotatable base, and combining the data to acquire three-dimensional geometric data of the inner surface of the split mold.

2. A device for generating reference geometric data for inspecting a tire by measuring a split mold, comprising:

a fixing base that carries the split mold for vulcanizing a tire, a measuring device that measures distances to an inner surface of the split mold in an inside diameter direction and in an axial direction, a computing device that generates data used in tire inspection by acquiring two-dimensional geometric data of the inner surface of the split mold over an entire circumference from the distances measured by the measuring device while rotating the measuring device, additionally acquiring two-dimensional geometric data of the inner surface of the split mold over the entire circumference across the split mold in the axial direction, and combining the data to acquire three-dimensional geometric data of the inner surface of the split mold.

3. A method for generating reference geometric data for tire inspection, comprising the steps of:

placing a split mold for vulcanizing a tire on a rotatable base to center the split mold, measuring distances to an inner surface of the split mold in an inside diameter direction and in an axial direction, acquiring two-dimensional geometric data of the inner surface of the split mold from the distances thus measured, and generating reference geometric data for tire inspection by further acquiring geometric data of the inner surface of the split mold over an entire circumference while rotating the rotatable base, and combining the data to acquire three-dimensional geometric data of the inner surface of the split mold.

4. A method for generating reference geometric data for tire inspection comprising the steps of:

placing a split mold for vulcanizing a tire on a rotatable base to center the split mold, measuring distances to an inner surface of the split mold over an entire circumference across the split mold in an inside diameter direction, acquiring two-dimensional geometric data of the inner surface of the split mold over the entire circumference from the distances thus measured, generating reference geometric data for tire inspection by further acquiring two-dimensional geometric data of the inner surface of the split mold over the entire circumference across the split mold in an axial direction, and combining the data to acquire three-dimensional geometric data of the inner surface of the split mold.

5. The device of claim 1, wherein the inner surface of the split mold is used to vulcanize the tire.

* * * * *